US006308711B1

(12) United States Patent
Goldberg

(10) Patent No.: US 6,308,711 B1
(45) Date of Patent: Oct. 30, 2001

(54) DENTAL PROTECTIVE EYE DEVICE

(75) Inventor: Michael Goldberg, San Pedro, CA (US)

(73) Assignee: Luminary Foundation, Los Angeles, CA (US)

( * ) Notice: Subject to any disclaimer, the term of this patent is extended or adjusted under 35 U.S.C. 154(b) by 0 days.

(21) Appl. No.: 09/390,857

(22) Filed: Sep. 3, 1999

(51) Int. Cl.[7] .................................................. A61F 9/00
(52) U.S. Cl. ................................................ 128/858; 2/447
(58) Field of Search .................................. 128/846, 857, 128/858; 2/436, 431, 439, 447, 452

(56) References Cited

U.S. PATENT DOCUMENTS

| | | | | |
|---|---|---|---|---|
| 1,188,679 | * | 6/1916 | Rextrew | 2/447 |
| 5,073,020 | * | 12/1991 | Lindberg | 351/106 |
| 5,297,298 | * | 3/1994 | Salatka | 2/447 |
| 5,413,119 | * | 5/1995 | Guerrant | 128/858 |
| 5,685,022 | * | 11/1997 | Essman | 2/447 |
| 6,023,791 | * | 2/2000 | Chiang | 2/441 |

* cited by examiner

Primary Examiner—Michael A. Brown
(74) Attorney, Agent, or Firm—Myers, Dawes & Andras LLP; Richard L. Myers

(57) ABSTRACT

The invention includes a protective eye device for an oral treatment patient including an eyepiece having bridge portions that form a seal with the nose. The bridge portions are a fulcrum between attachment portions that extend downwardly and outwardly from the bridge portions, and upper portions disposed above the bridge portions. A retaining member is coupled to the attachment portions below the fulcrum such that tension on the retaining member causes the attachment portions to extend toward the face and facilitates the sealing relationship between a lower rim and a middle surface of the face between the eyes and mouth. The tension on the retaining member simultaneously causes the upper portions to extend away from the face, and facilitates the spatial relationship, or a gap, between the forehead and an upper rim. The invention also includes a method for shielding the eyes of a patient.

13 Claims, 4 Drawing Sheets

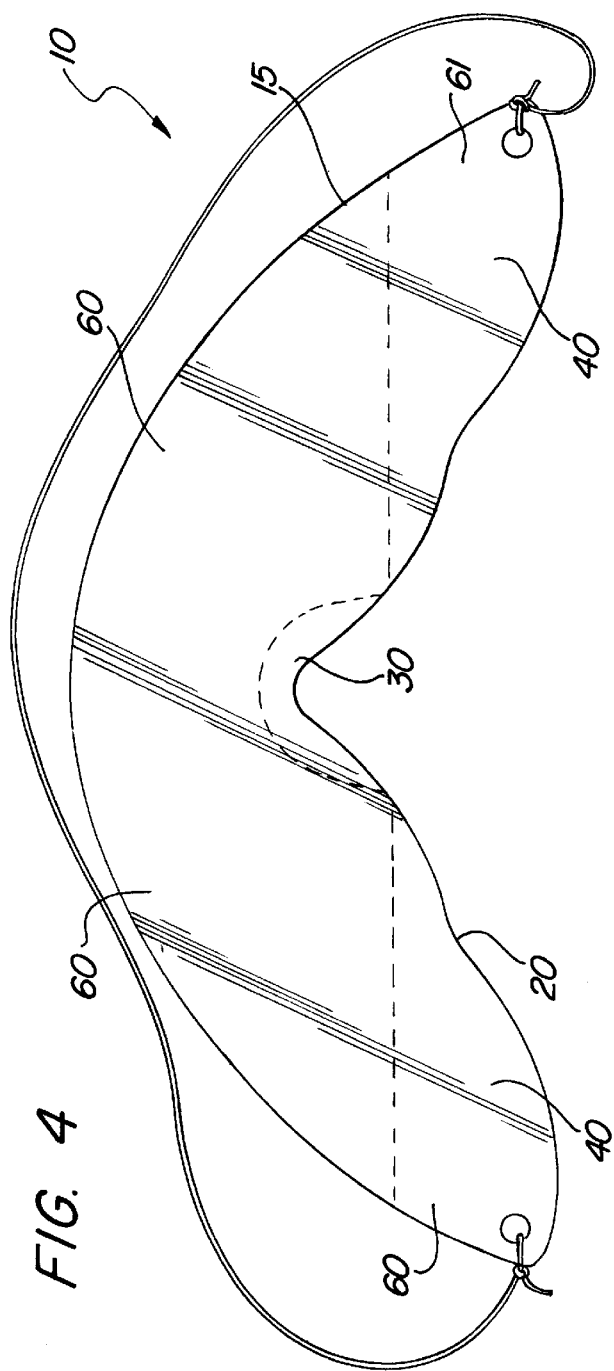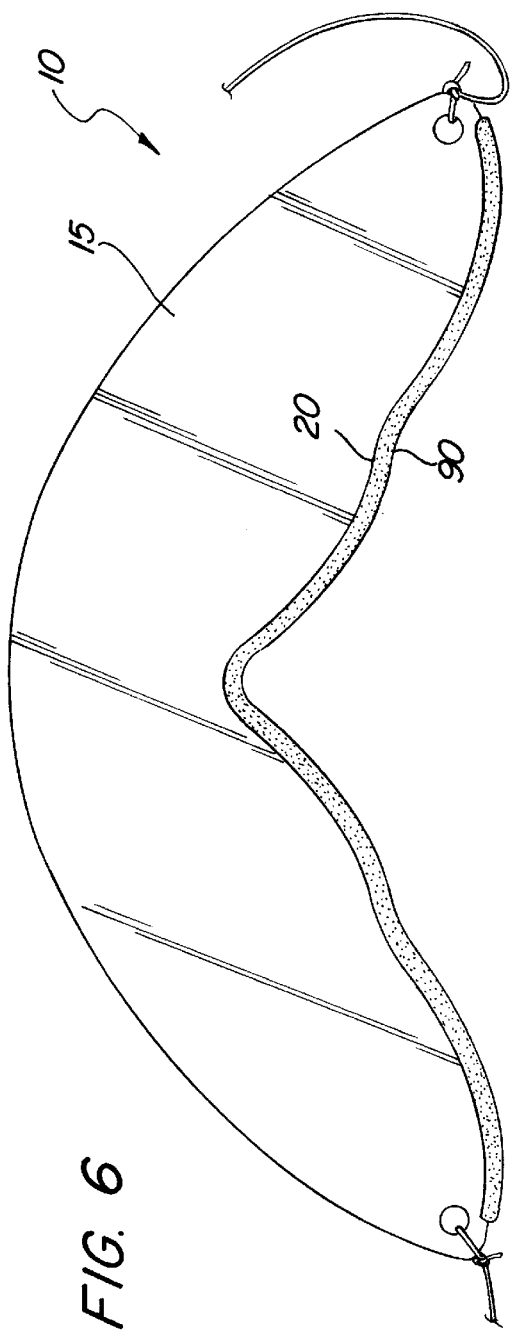

DENTAL PROTECTIVE EYE DEVICE

BACKGROUND OF THE INVENTION

1. Field of the Invention

The invention relates generally to protective eye devices for patients receiving oral treatment, and more specifically to eye protectors for dental patients.

2. Description of Related Art

Patients receiving oral treatment often expose their eyes to harm. Whether the treatment is dental, orthodontic or surgical, treating physicians often work with highly sharp objects that require precision handling. A slight mishandling of a sharp instrument may cause permanent eye damage to the patient.

In addition to handling sharp objects, oral physicians typically work with a variety of materials and chemicals, all of which are handled within inches of the exposed eyes of a patient. For example, orthodontists commonly handle metals wires, brackets, and epoxy. Dentists often apply chemicals to the mouth. If spilled such chemicals can easily reach the eyes and cause severe damage. Even a routine dental cleaning involves many procedures, such as scrubbing with a brush and suctioning with a tube, that can cause fluids and other debris to splatter into the patient's eyes.

Despite these hazards, practitioners commonly do not require or even invite their patients to wear some type of protective device. This also makes the practitioner's job more difficult and stressful as he or she must exercise extreme care and precision in handling instruments, materials and chemicals. Practitioners also subject themselves and their businesses to potential liability resulting from lack of protection for the patient's eyes.

The prior art includes protective eye devices which are heavy and bulky and consequently uncomfortable for the patient. Furthermore, prior art devices are expensive to manufacture and, thus, are not disposable. This leaves patients exposed to infection from contaminated eye devices which have been used repeatedly.

Representative of this art is U.S. Pat. No. 5,413,119 (Guerrant), which discloses a frame with a shield and a strap secured to the frame at substantially the same level as the inferior apex of the frame. A slight horizontal distance is shown between the wearer's forehead and the superior rim of the frame.

SUMMARY OF THE INVENTION

In accordance with the present invention, a structure and associated method are disclosed which overcome these deficiencies in protecting the eyes of a patient receiving oral treatment. Though the preferred embodiment is a protective eye device for a dental patient, the invention may apply to different types of patients receiving varying oral treatment.

Structurally, the invention is a protective eye device adapted to be worn by a dental patient having a head and a face with eyes, a nose, a mouth, and a forehead. The protective eye device comprises an eye shield and a retaining member. The eye shield, or eyepiece, has an upper rim and a lower rim with bridge portions and attachment portions disposed between the upper and lower rim. The lower rim is adapted to form a seal, or establishes a sealing relationship, with the face of the patient. More specifically, the lower rim is configured to form a seal with a middle surface of the patient's face between the eyes and the mouth.

The bridge portions of the eye shield are disposed centrally of the eye shield, and are adapted to form a seal with the nose of the patient. The attachment portions of the eye shield are disposed outwardly and downwardly from the bridge portion. With this configuration, the bridge portions function as a pivot or fulcrum, with the attachment portions of the eye shield disposed below the fulcrum, and the upper portions of the eye shield disposed above the fulcrum.

The retaining member is coupled to the attachment portions of the eye shield in proximity to the lower rim and below the bridge portions. When the eye protector is operatively disposed on the face of the patient, tension on the retaining member initiates a lever action. As the attachment portions are drawn against the face of the patient, the eye shield tends to pivot on the fulcrum facilitating a sealing relationship between the lower rim and the face of the patient, while facilitating a spatial relationship between the upper rim and the face of the patient. This spatial relationship creates a gap between the forehead and the upper portions of the eye shield. The retaining member may be a strap, or a pair of arms with hooks adapted to secured behind the ears of the patient.

As a result of the retaining member being secured to attachment portions of the eye shield which are below the fulcrum, tension on the retaining member pulls the attachment points toward the face such that the upper portions of the eye shield extend away from the face. The eye protective device may include a cushion disposed along the lower rim of the eye shield to facilitate formation of the seal.

The eye shield may be sterilized and adapted to be disposable after a single usage. The eye shield may comprise a rigid material or a flexible material. If the eye shield is made of a flexible material, such as flexible thin plastic, tension on the retaining member will also pull a left side and a right side of the eye shield against the head and around the eyes of the patient.

The invention may simply include the eyepiece, or eye shield, alone. The eyepiece has an upper rim adapted to be operatively disposed in a spatial relationship with the face, and a lower rim adapted to operatively disposed in a sealing relationship with a middle surface of the face between the eyes and the mouth. The lower rim has a nose portion adapted to be secured against the nose. The eyepiece further comprises at least one attachment point for a retaining member, the attachment point being disposed below the nose portion of the lower rim such that the nose portion functions as a fulcrum between the lower rim and the upper rim. The upper rim is spaced apart and away from the forehead. The lower rim further comprises outer portions disposed outwardly and downwardly from the nose portion. In an operative position, the outer portions of the lower rim are curved toward and against the face. The eyepiece may comprise a flexible material or a rigid material. The eyepiece has a horizontal radius of curvature that increases from the lower rim to the upper rim.

The invention also includes a method for shielding the eyes of a face, the face having a nose, a forehead, and a mouth. The method comprises the steps of providing an eyepiece having an upper rim, a lower rim, bridge portions disposed centrally and between the upper rim and the lower rim, upper portions disposed above the bridge portions, and bottom portions disposed below the bridge portions; sealing a middle surface of the face between the eyes and the mouth with the lower rim of the eyepiece; coupling a retaining member to the bottom portions of the eyepiece; and pivoting the eyepiece at the bridge portions by moving the bottom portions of the eyepiece toward the face while moving the upper portions of the eyepiece away from the face.

The step of pivoting the eyepiece further includes opening a gap between the upper rim and the forehead.

The method further comprises the steps of disposing a cushion along the lower rim of the eyepiece as well as sterilizing the eyepiece.

The method further includes providing a previously unworn eyepiece. Therefore, each eyepiece may simply be thrown away after a single usage.

Many benefits result from this invention. The sterilization and disposability of the invention offers great advantages in that each eye protective device may simply be worn once and thrown away without great expense. Practitioners need not involve themselves with sterilization as each protective eye device is simply thrown away after one use. Furthermore, practitioners may perform their procedures more easily without fear of damaging the patient's eyes. The patient may undergo treatment more confidently knowing that his or her eyes are now well protected.

The entire eye protective device is very lightweight making it convenient and comfortable for a patient to use. Since the eyepiece wraps around the eyes of the patient, it protects the eyes from any matter which might otherwise enter from the front or the sides of the face.

In one aspect, the invention includes a protective eye device for an oral treatment patient comprising an eyepiece having bridge portions that form a seal with the nose. The bridge portions are a fulcrum between attachment portions that extend downwardly and outwardly from the bridge portions, and upper portions disposed above the bridge portions. A retaining member is coupled to the attachment portions below the fulcrum such that tension on the retaining member causes the attachment portions to extend toward the face and facilitates the sealing relationship between a lower rim and a middle surface of the face between the eyes and mouth. The tension on the retaining member simultaneously causes the upper portions to extend away from the face, and facilitates the spatial relationship, or a gap, between the forehead and an upper rim. The invention also comprises a method for shielding the eyes of a patient.

As used herein, words such as "upward" and "downward" which are used to describe directions, describe directions referring to the eye protector operatively disposed on the head of a patient. Thus, the "upward" direction is toward the forehead of the patient and away from the neck of the patient. In contra-distinction, "downward" refers to a direction toward the neck of the patient and away from the forehead of the patient. The word "outward" refers to directions away from the nose of the patient and toward the side of the patient's head.

The invention, now having been briefly summarized, may be better visualized by turning to the following drawings wherein like elements are referenced by like numerals.

BRIEF DESCRIPTION OF THE DRAWINGS

FIG. 4 is a front elevation view of the eye protector disposed in a flattened form;

FIG. 6 is a front elevation view similar to FIG. 4 and illustrating a further embodiment having a cushion strip disposed along the lower rim of the eye protector.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS

Figure 1:
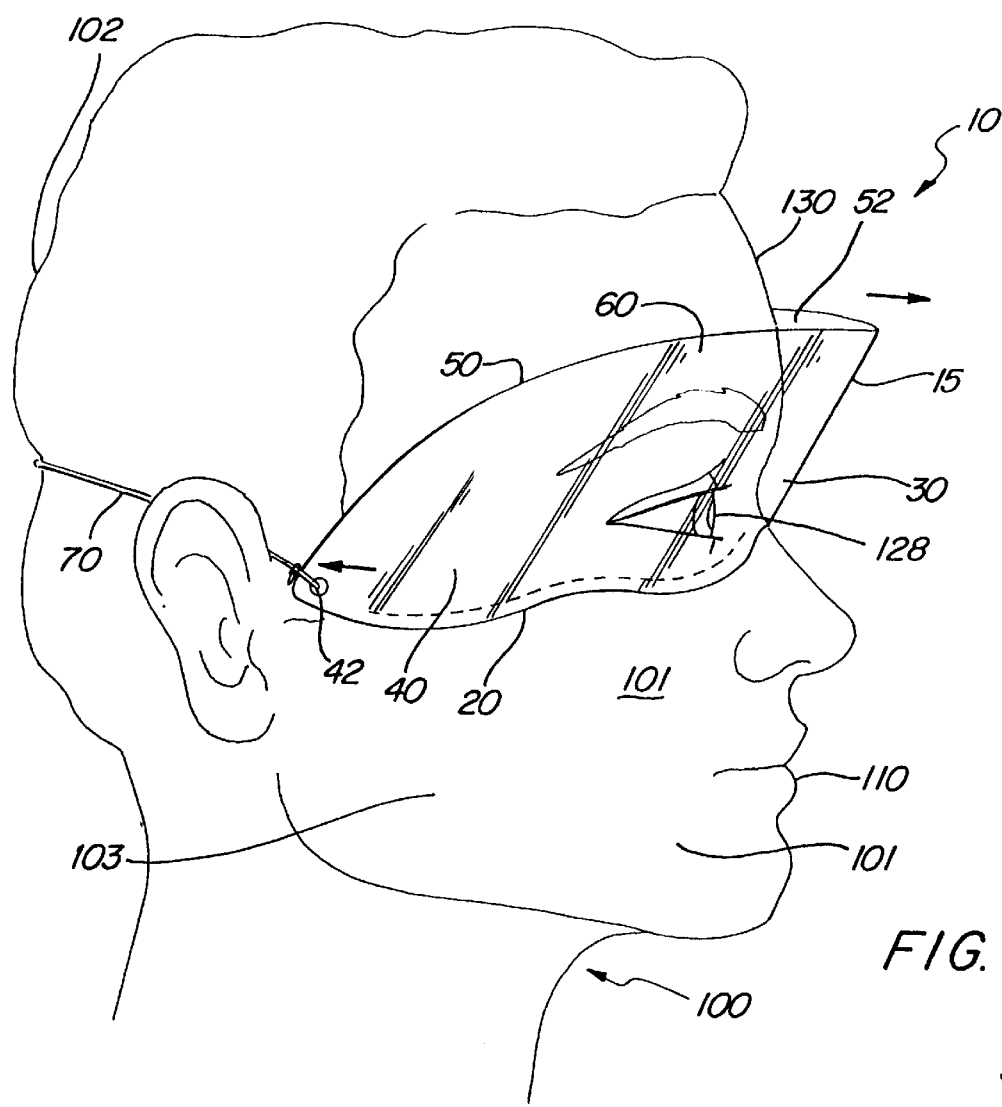
FIG. 1 is a perspective view of an embodiment of the eye protector of the present invention operatively positioned on the face of a dental patient in a prone position.
Figure 2B:
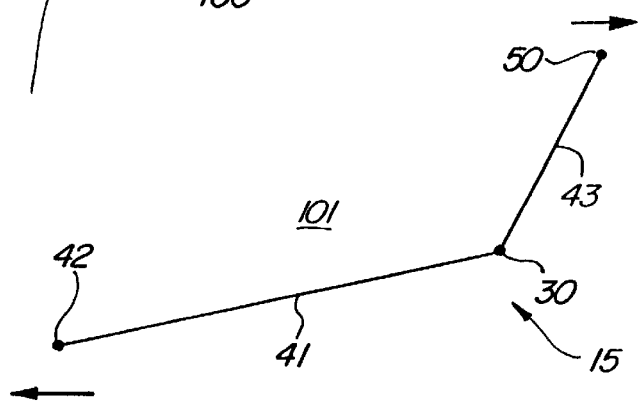
FIG. 2b is a schematic diagram illustrating a lever action associated with the eye protector.
Figure 2A:
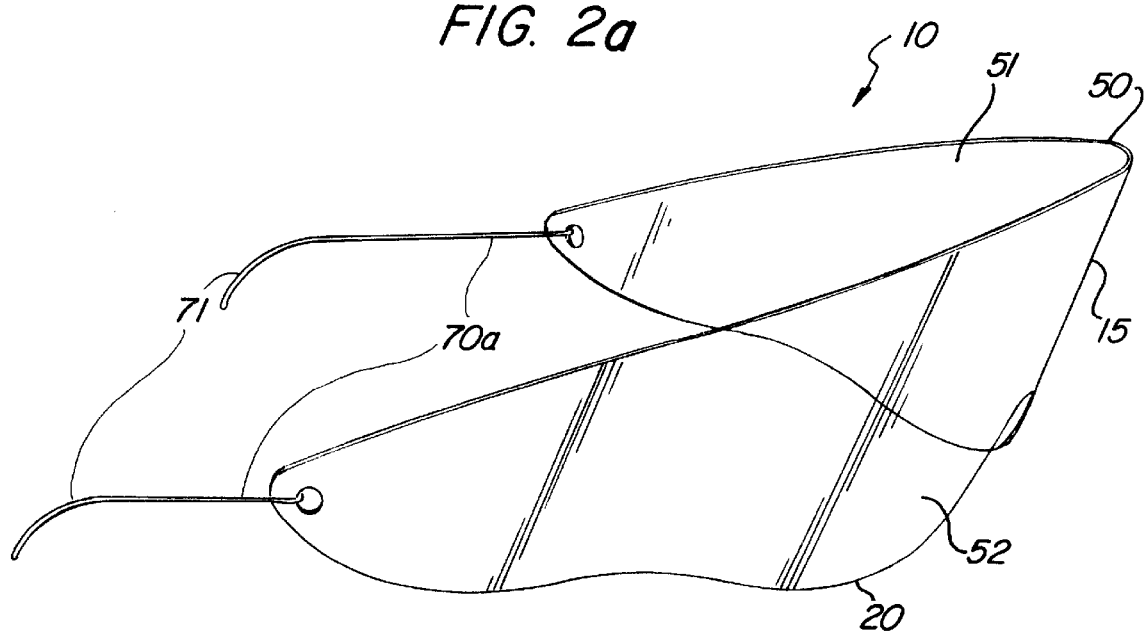
FIG. 2a is a perspective view of the eye protector disposed in a operative, curved configuration.

A protective eye device or eye protector according to the present invention is illustrated in FIG. 1 and designated generally by the reference numeral 10. FIG. 1 is an environmental side view of the eye protector 10 as worn by a patient 100 having a face 101. The patient 100 may be a dental patient or any other patient receiving oral treatment, including orthodontic or surgical treatment. FIG. 2a is a side perspective view of the eye protector 10, shown in an operative, curved configuration.

Figure 3:
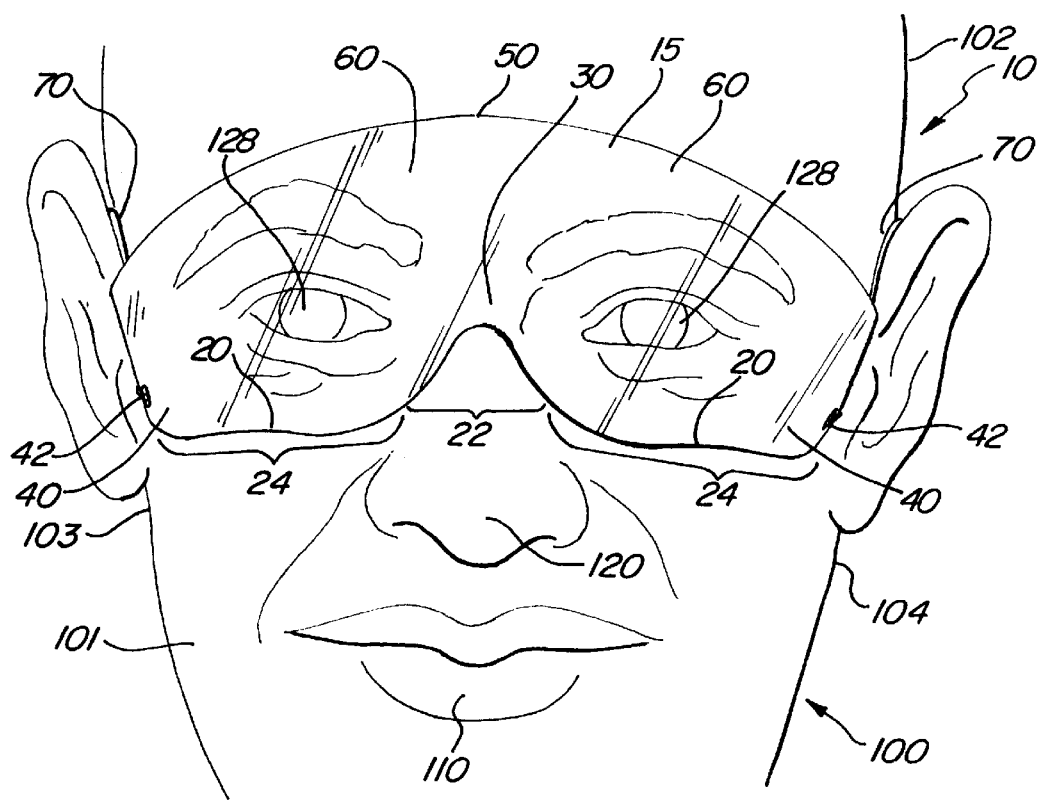
FIG. 3 is a front elevation view of the eye protector operatively disposed on the face of the patient.
Figure 5:
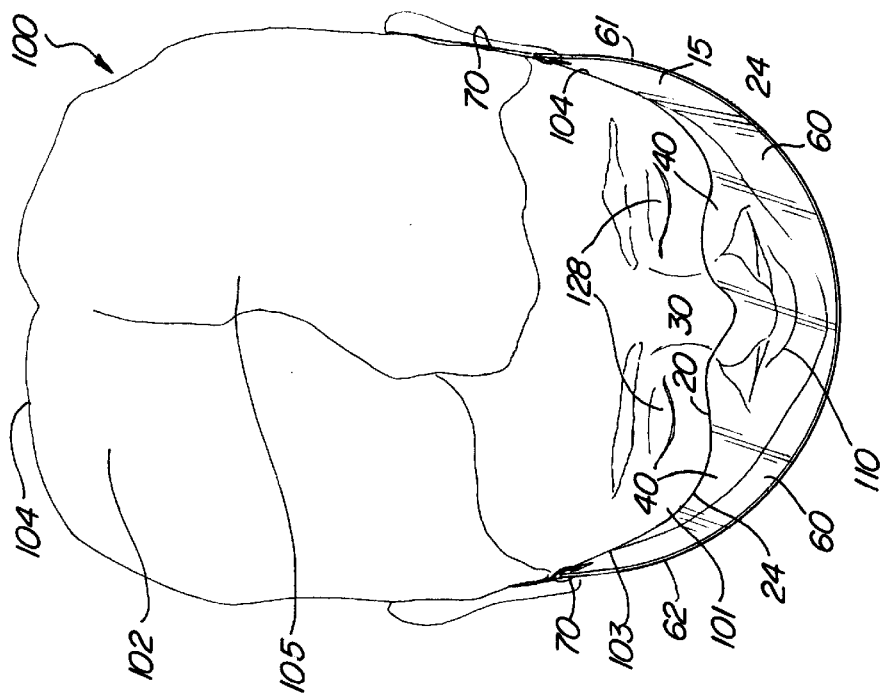
FIG. 5 is an top plan view of the eye protector operatively disposed on the head of a patient.

FIG. 3 is an front elevation view of the invention 10 as worn by the patient 100. The protector 10 comprises an eye shield, or eyepiece, 15 with a retaining member 70. The eye shield 15 has an upper rim 50 and a lower rim 20. The eye shield 15 also has bridge portions 30 and attachment portions 40 disposed between the upper rim 50 and the lower rim 20. The bridge portions 30 are disposed centrally and adapted to form a seal with the nose 120 of the patient 100. The bridge portions 30 of the eye shield 15 include a nose portion 22 of the lower rim 20 that is adapted to establish a sealing relationship with the nose 120. More specifically, the nose portion 22 of the lower rim 20 is sealed with or secured against the nose 120. The lower rim 20 also includes outer portions 24 that extend downwardly and outwardly from the nose portion 22 toward the sides 103, 104 of the face 101. In an operative position as shown in FIG. 5, the outer portions 24 of the lower rim 20 are curved toward and against the face 101. The lower rim 20 substantially seals a middle surface of the face 101 of the patient 100 between the eyes 128 and the mouth 110.

The eyepiece 15 further comprises two attachment portions 40 disposed below the bridge portions 30, and upper portions 60 disposed above the bridge portions 30. The attachment portions 40 are disposed outwardly and downwardly from the bridge portions 30. Each attachment portion 40 has an attachment point 42 that is also below the bridge portions 30 and in proximity to the lower rim 20. A retaining member 70, such as a strap or a pair of arms, is coupled to the attachment portions 40 at the attachment points 42.

Turning now to FIG. 1, it will become apparent that when the protective eye device 10 is worn, the bridge portions 30 of the eyepiece 15 is a fulcrum between the lower attachment portions 40 and the upper portions 60. Therefore, the bridge portions 30 tend to function as a fulcrum between the upper rim 50 and the lower rim 20.

When a patient 100 puts on the protective eye device 10 by engaging the retaining member 70 with his or her head 102, tension will be applied to the retaining member 70. More specifically, the retaining member 70 will exert force or tension in the direction towards the back 104 of the head 102. Since the retaining member 70 is coupled to the attachment portions 40 via attachment points 42, which are all below the fulcrum 30, tension on the retaining member 70 causes the attachment portions 40 of the eye shield 15 to extend toward the face 101 while simultaneously causing the upper portions 60 disposed above the fulcrum 30 to extend away from the face 101. This tension acting beneath the fulcrum 30 facilitates the sealing relationship between the lower rim 20 and the face 101, as well as the spatial relationship between the upper rim 50 and the face 101. More specifically, a seal is formed by the lower rim 20 against a middle surface of the face 101 between the eyes 128 and the mouth 110, and a gap 52 is defined between the upper portions 60 and the forehead 130 of the patient 100. The gap 52 between the forehead 130 and the eye shield 15 is greatest at the upper rim 50 of the eye shield 15. Thus, the upper rim 50 is spaced apart and away from the forehead 130.

FIG. 2a is a side perspective view of the eye protector 10 disposed in an operative, curved form. The eyepiece 15 itself may be a rigid structure comprising a hard material such as hard plastic. FIG. 2b is a schematic diagram showing the operation of the invention from a side view. In FIG. 2b, the eyepiece 15 itself is a lever turning on the fulcrum, or bridge portions, 30. The line, or distance, between the attachment point 42 to the bridge portions, or fulcrum, 30 is a pulling portion 41 of the lever. The line, or distance, between the shield 30 and the upper rim 50 is a pushing portion 43 of the lever. As attachment point 42 is pulled by the retaining member (not shown) toward the face 101 as illustrated by the bottom arrow, the pulling portion 41 of lever 15 is being pivoted toward the face 101, simultaneously causing the pushing portion 43 of lever 15 and the upper rim 50 to extend away from the face 101, as illustrated by the top arrow.

FIG. 2a also illustrates an alternative embodiment of the retaining member 70. In FIG. 2a, the retaining member comprises two arms 70a, each having a hook 71 adapted to wrap around an ear of the patient.

Though the eyepiece 15 may comprise frames, the eyepiece 15 in the preferred embodiment shown in FIG. 2a is a single, integral piece without frames. FIG. 2a also illustrates the shape of the eye protective device 10 when worn by the patient. The result in FIG. 2a is a semi-conical shape having a larger radius of curvature at the upper rim 50 than at the lower rim 20. Eyepiece 15 also has an inner surface 51 that is vertically parallel with an outer surface 52.

FIG. 4 is a front elevation view of the invention in flattened form. The eyepiece 15 can be made of a flexible substance, such as a thin, flexible plastic film, which assumes a flat shape when unworn and a bent shape when worn. When the eye protective device 10 has not yet been worn, its flattened shape allows for efficient storage. Being made of a flexible material, the eyepiece 15 bends and conforms to the shape of the wearer's face, thus forming a custom fit seal between the lower rim 20 and the face of each individual patient. In FIG. 3, the flexibility of the eyepiece 15 allows it to conveniently wrap around any patient's face, be it wide or narrow. Thus, the lower rim 20 is adapted to seal a middle surface of any type of face between the eyes, on the one hand, and the mouth and nose, on the other hand.

When the eyepiece is made of a flexible material, the bridge portions 30 not only function as a fulcrum between the upper portions 60 and the lower attachment portions 40 as shown in FIG. 3, but it also becomes the flexure point from which the left side 61 and the right side 62 of the eyepiece 15 turn and extend toward the face 101 as shown in FIG. 5. Thus, the eyepiece 15 not only protects the eyes 128 from matter which might otherwise enter from the front side of the face 101 as shown in FIG. 3, but it also wraps around the eyes 128 to protect them from any matter which would otherwise enter from the sides 103, 104 of the face 101, as shown in FIGS. 1 and 5. Therefore, in FIG. 5, tension on the retaining member 70 not only exerts force on the attachment portions 40 of eyepiece 15 toward the back 104 of the patient's head 102, but it also exerts force on attachment portions 40 the eyepiece 15 toward the center 105 of the head 102, causing the eyepiece 15 to wrap around the patient's face 101.

The eyepiece may be made in a variety of sizes to accommodate men, women and children. Furthermore, the eyepiece may include different colored tints and various degrees of shading so as to reduce glare. The eyepiece may comprise a single solid color, or a mix of different colors, such as a striped or wavy rainbow design. Being made from an inexpensive material such as plastic, the entire eye device is inexpensive, and therefore disposable. The eyepiece may also be sterilized.

The sterilization and disposability of the eye protector 10 offers great advantages in that each protector 10 may simply be worn once and thrown away without great expense. Since a patient may wear a brand-new, sterilized eye protector 10 each time he or she visits a practitioner, the protector 10 eliminates any potential for contamination due to prior used devices. Practitioners need not involve themselves with sterilization as each protector 10 is simply thrown away after one use. Furthermore, practitioner may perform his/her procedure more easily without fear of damaging the patient's eyes; and while the patient may undergo treatment more confidently knowing that his/her eyes are now well protected.

Figure 7:
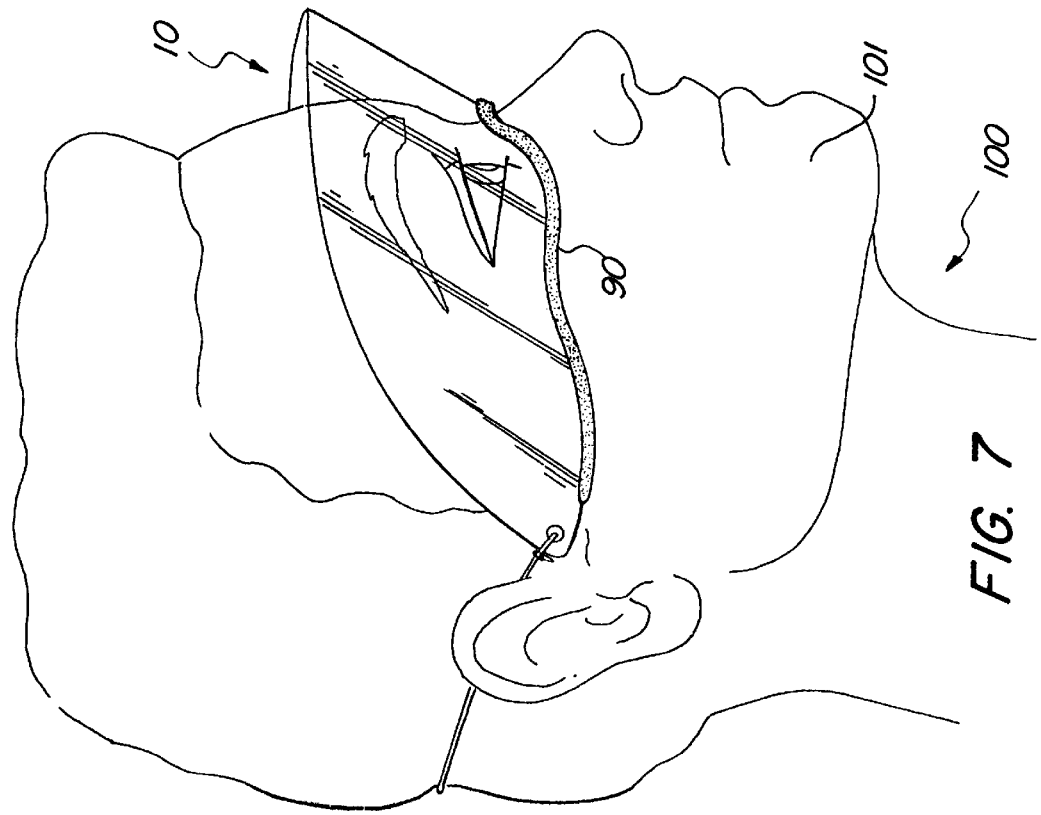
FIG. 7 is a perspective view of the further embodiment in FIG. 6 operatively positioned on the face of the dental patient in a prone position.

FIG. 6 is a front elevation view of an alternate embodiment of the invention 10 in flattened form. In FIG. 6, the eye protective device 10 comprises a cushion 90 disposed along the lower rim 20 of the eyepiece 15. When worn by a patient 100 as shown in FIG. 7, the cushion 90 thus forms a seal with the face 101 of the patient 100, as opposed to the lower rim 20 sealing the face 101 as shown in FIG. 1. In the preferred embodiment, cushion 90 comprises plastic foam.

Many alterations and modifications may be made by those having ordinary skill in the art without departing from the spirit and scope of the invention. Therefore, it must be understood that the illustrated embodiments have been set forth only for the purposes of example and that it should not be taken as limiting the invention as defined by the following claims. The claims are thus to be understood to include what is specifically illustrated and described above, what is conceptionally equivalent, what can be obviously substituted and also what essentially incorporates the essential idea of the invention.

I claim:

1. A protective eye device adapted to be worn by a dental patient having a head and a face with eyes, a nose, a mouth, and a forehead, the protective eye device comprising:

an eye shield devoid of any supporting frame and having an upper rim and a lower rim with bridge portions and attachment portions disposed between the upper rim and the lower rim, the lower rim being adapted to form a sealing relationship with the face of the dental patient;

the bridge portions of the eye shield being disposed centrally and being adapted to form a seal with the nose of the patient;

the attachment portions of the eye shield being disposed outwardly and downwardly from the bridge portions; and a retaining member coupled to the attachment portions of the eye shield in proximity to the lower rim and below the bridge portions such that tension on the retaining member will pivot the bridge portions of the eye shield on the nose of the patient to facilitate a sealing relationship between the lower rim and the face of the patient and to facilitate a spaced relationship between the upper rim and the face of the patient.

2. The protective eye device of claim 1, wherein:

the bridge portions of the eye shield function as a fulcrum;

the attachment portions of the eye shield are disposed below the fulcrum; and upper portions of the eye shield are disposed above the fulcrum.

3. The protective eye device of claim 2 wherein the tension on the retaining member pulls the attachment portions of the eye shield toward the face such that the upper portions of the eye shield pivot away from the face.

4. The protective eye device of claim 1 wherein the retaining member is an elastic strap.

5. The protective eye device of claim 1 further comprising a cushion disposed along the lower rim of the eye shield.

6. The protective eye device of claim 1 wherein the eye shield is sterilized.

7. The protective eye device of claim 1 wherein the eye shield comprises a flexible material.

8. A method for shielding eyes of a face, the face having a nose, a forehead, and a mouth, the method comprising the steps of:

providing an eyepiece having an upper rim, a lower rim, bridge portions disposed centrally and between the upper rim and the lower rim, upper portions disposed above the bridge portions, and bottom portions disposed below the bridge portions;

sealing a middle surface of the face between the eyes and the mouth with the lower rim of the eyepiece;

coupling a retaining member to bottom portions of the eyepiece;

tensioning the retaining member to bend the eyepiece along a curve of generally constant radius; and during the tensioning step, pivoting the eyepiece at the bridge portions by moving the bottom portions of the eyepiece toward the face while moving the upper portions of the eyepiece away from the face.

9. The method of claim 8 wherein the step of pivoting the eyepiece further comprises the step of opening a gap between the upper rim and the forehead.

10. The method of claim 8 further comprising the step of disposing a cushion along the lower rim of the eyepiece.

11. The method of claim 8 further comprising the step of sterilizing the eyepiece.

12. A method for creating a barrier between the mouth and the eyes of a dental patient, comprising the steps of:

providing an eye shield with a bridge portion, attachment portions, and a retaining member, the eye shield having a generally planar configuration and a generally curved configuration;

storing the eye shield in the generally planar configuration;

placing the eye shield on the face the patient with the bridge portions in contact with the nose of the patient;

bending the eye shield from the generally planar configuration to the generally curved configuration;

tensioning the retaining member around the head of the patient to pivot the bridge portions on the nose of the patient;

during the tensioning step placing the lower rim in a sealing relationship with the face of the patient; and during the tensioning step placing the upper rim in a spaced relationship with the face of the patient.

13. The method recited in claim 12 wherein the face shield in the curved configuration has a generally constant radius.

\* \* \* \* \*